United States Patent
Rezaie

(10) Patent No.: US 11,854,381 B2
(45) Date of Patent: Dec. 26, 2023

(54) COUPLING OF FOOT SWITCH AND MEDICAL DEVICE

(71) Applicant: OLYMPUS WINTER & IBE GmbH, Hamburg (DE)

(72) Inventor: Hamid Rezaie, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 317 days.

(21) Appl. No.: 17/216,966

(22) Filed: Mar. 30, 2021

(65) Prior Publication Data

US 2021/0304590 A1 Sep. 30, 2021

(30) Foreign Application Priority Data

Mar. 30, 2020 (DE) ...................... 10 2020 108 701.2

(51) Int. Cl.
| | |
|---|---|
| G08C 17/04 | (2006.01) |
| A61B 17/32 | (2006.01) |
| A61B 18/12 | (2006.01) |
| A61B 18/20 | (2006.01) |
| H04B 5/00 | (2006.01) |
| A61B 17/00 | (2006.01) |

(52) U.S. Cl.
CPC ...... *G08C 17/04* (2013.01); *A61B 17/320068* (2013.01); *A61B 18/1206* (2013.01); *A61B 18/20* (2013.01); *H04B 5/0025* (2013.01); *H04B 5/0068* (2013.01); *A61B 2017/00973* (2013.01)

(58) Field of Classification Search
CPC .... G08C 17/02; G08C 17/04; G08C 2201/20; H04W 4/80; A61B 17/320068; A61B 2017/00973; H04B 5/0025
See application file for complete search history.

(56) References Cited

U.S. PATENT DOCUMENTS

| | | | |
|---|---|---|---|
| 8,489,021 B2 * | 7/2013 | Granqvist | ............ A61B 5/0002 455/100 |
| 2009/0121865 A1 | 5/2009 | Hamel et al. | |
| 2016/0174018 A1 | 6/2016 | Schönewerk | |
| 2020/0160141 A1 * | 5/2020 | Soriano | ............ G06K 19/07327 |
| 2021/0007760 A1 * | 1/2021 | Reisin | ................ A61B 17/3207 |

FOREIGN PATENT DOCUMENTS

| | | |
|---|---|---|
| DE | 10 2008 039 156 A1 | 2/2010 |
| DE | 10 2014 113 273 A1 | 3/2016 |
| EP | 1 629 786 A2 | 3/2006 |
| WO | 2019/173574 A1 | 9/2019 |

* cited by examiner

*Primary Examiner* — Vernal U Brown
(74) *Attorney, Agent, or Firm* — Scully, Scott, Murphy & Presser, P.C.

(57) ABSTRACT

A system including: a foot switch for controlling a medical device; and a receiver for the medical device to be controlled as components. Where the foot switch and the receiver are configured for wirelessly transmitting uniquely assignable control signals after completion of coupling at least from the foot switch to the receiver; one of the components comprises an NFC read module for reading out a transponder in a vicinity and an other component comprises the transponder that can be read out by the NFC read module; and the NFC read module is configured at least to initiate the coupling of the foot switch and the receiver on the basis of items of information read out from the transponder.

10 Claims, 2 Drawing Sheets

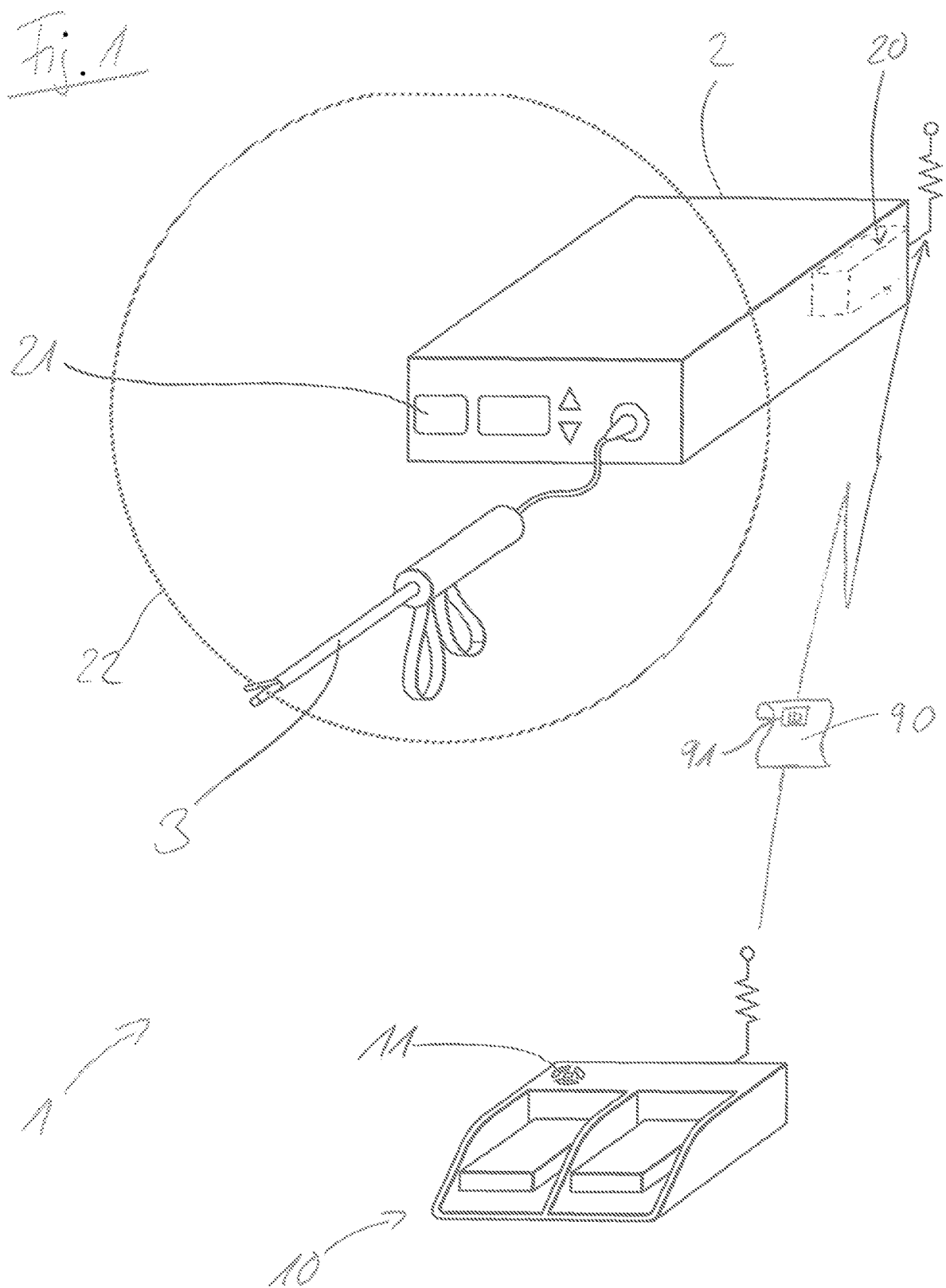

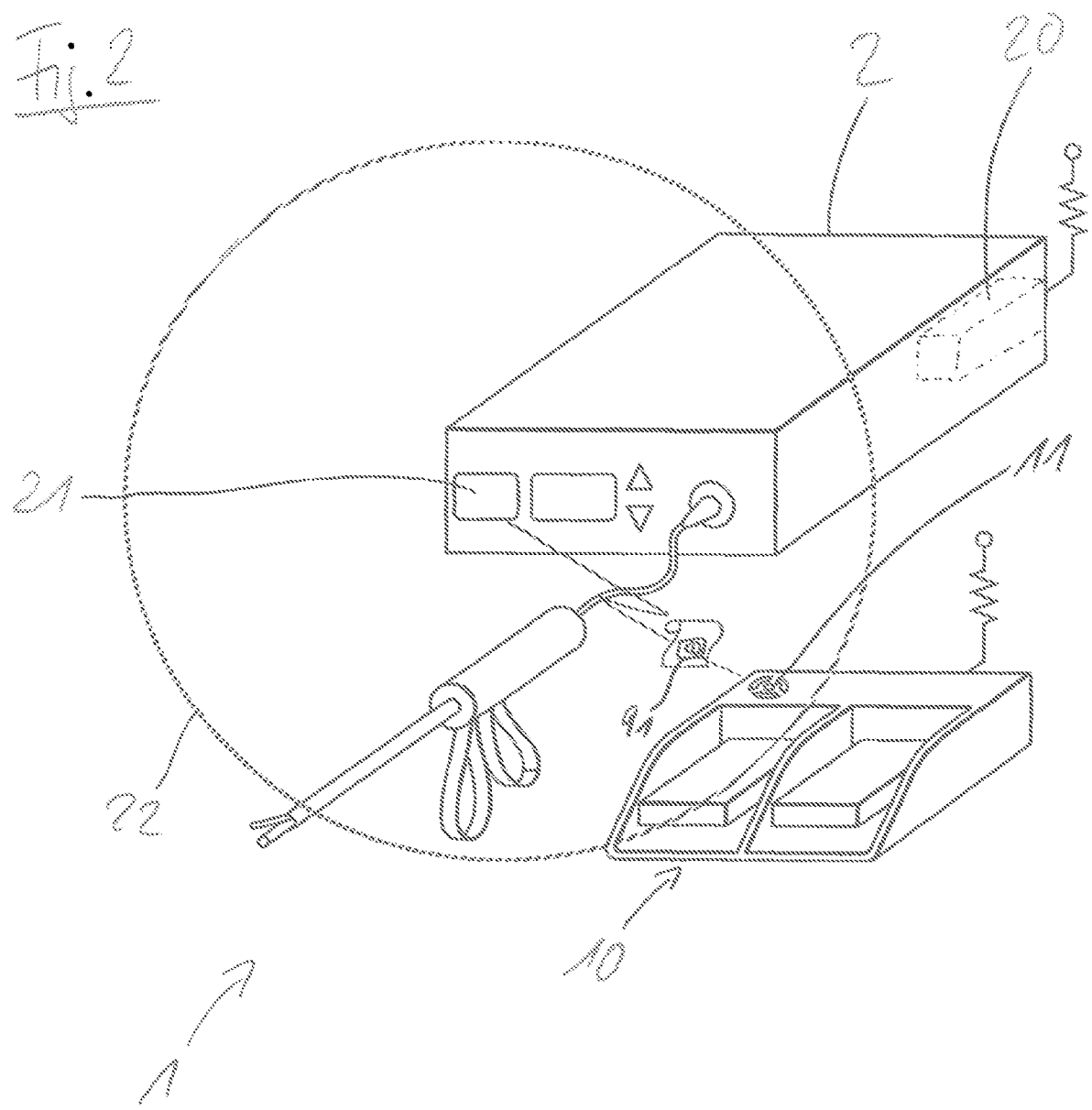

COUPLING OF FOOT SWITCH AND MEDICAL DEVICE

CROSS-REFERENCE TO RELATED APPLICATIONS

The present application is based upon and claims the benefit of priority from DE 10 2020 108 701.2 filed on Mar. 30, 2020, the entire contents of each of which are incorporated herein by reference.

BACKGROUND

Field

The present disclosure relates to a system comprising a foot switch for controlling a medical device and a receiver connected to the medical device to be controlled, and a method for coupling foot switch and receiver.

Prior Art

In medical technology, foot switches are routine for controlling medical devices. It is possible by way of foot switches, for example, to control the activation state of a handheld instrument, without the guiding hand itself or even only one finger thereof having to be moved for this purpose. The medical personnel can thus concentrate solely on guiding the instrument by hand and control the activation state of the instrument by foot disengaged therefrom. The activation state does not have to be restricted here to switching on and off a specific function of the handheld instrument, but rather can also comprise continuous adjustability. Examples of medical devices having corresponding foot control are dental instruments, such as drills, HF generators for high-frequency surgery, ultrasound generators for ultrasonic scalpels, and/or laser systems.

Foot switches can be connected to the medical device to be controlled via cable. So as not to restrict or obstruct the freedom of movement of the medical personnel, for example in an operating room, however, foot switches are also known which transmit wireless control signals to the medical device to be controlled. A suitable receiver for the control signals then either has to be integrated directly into the medical device, or a suitable external receiver is to be provided at the signal input, to which, for example, a wired foot switch can also be connected.

In order to ensure that actually only a specific medical device is controlled using a foot switch, it is absolutely necessary to couple the foot switch uniquely to a receiver in such a way that the control signals emitted by the foot switch are exclusively processed by the coupled receiver. For this purpose, the control signals normally contain a unique code, which uniquely identifies the control signals as coming from a specific foot switch. This is described correspondingly, for example, in EP 1 629 786 A1.

The free coupling of a foot switch to a specific receiver, independently of whether it is configured as an external unit or integrated into a medical device to be controlled, is frequently not provided in the prior art or is only possible with great complexity, so that generally in principle a one-to-one assignment exists of a foot switch to a medical device thus to be controlled, or at least to a specific receiver unit.

SUMMARY

An object is to provide a system and a method, in which a foot switch can be coupled in a simple manner to a receiver to control a medical device.

Accordingly, a system is provided. The system comprising a foot switch for controlling a medical device and a receiver connected to the medical device to be controlled as components, wherein the foot switch and the receiver are configured for wirelessly transmitting uniquely assignable control signals after completed coupling at least from the foot switch to the receiver, wherein one of the components comprises an NFC read module for reading out a transponder in the vicinity and the other component comprises a transponder that can be read out by the NFC read module, and wherein the component comprising the NFC read module is configured at least to initiate the coupling of foot switch and receiver on the basis of items of information read out by the transponder.

Also provided is a method for coupling a foot switch for controlling a medical device and a receiver for the medical device to be controlled by a system, the method comprising:
 a) initiating the coupling between the foot switch and the receiver by moving the foot switch toward the receiver, so that the transponder of the one component is located in the vicinity of the NFC read module of the other component; and
 b) waiting until the items of information required for coupling are exchanged and the coupling is completed.

Firstly, several terms used in conjunction with the embodiments will be explained.

"Coupling" refers to initially establishing a connection between two components, during which items of information are exchanged which are required for establishing a one-to-one connection between the two components. The items of information exchanged for the coupling can also contain data to secure the following connection between the two components by signing or encrypting the data exchange.

"Near Field Communication" (NFC) refers to wireless data communication, the range of which is technically limited to short distances of a few centimeters. Thus, for example, in the international NFC transmission standard of the same name, the contactless exchange of data by electromagnetic induction between two coils making use of RFID technology, such as having passive transponders, is provided. Due to the short range of the data transfer, it is hardly possible for data exchanged via NFC to be tapped by third parties.

An "NFC read module" is a module for reading out items of information from a suitable transponder which is located in the vicinity of the read module, so that the near field communication, to which the read module is restricted, can take place.

Control signals are "uniquely assignable" if they have a characteristic which enables a receiver of the signals to establish that a control signal was emitted by a specific transmitter or at least by the same transmitter as another control signal. In the case of wirelessly transmitted control signals, this characteristic can include properties of the wireless transmission (for example frequency, modulation, etc.). However, the control signal itself can have an identification as a characteristic, for example in the form of an identification number and/or identification character string uniquely identifying the transmitter or by electronic signature of the transmitted control signal using a uniquely assignable key.

A practically arbitrary coupling of a foot switch to a receiver connected to a medical device is simple and can be secure if the coupling is at least initiated by a near field communication. Since a corresponding near field communication is only possible at short range (i.e., the two devices to be coupled have to be arranged physically close to one another for the coupling), on the one hand, it is fundamentally ensured that the foot switch is also actually coupled to the desired receiver and not, for example, to a receiver arranged farther away, and on the other hand, undesired tapping by third parties of the items of information exchanged at least for the initiation of the coupling is practically precluded due to the inherent properties of near field communication.

In order to at least initiate the coupling, at least one of the two components of a system comprising a foot switch and a receiver can be equipped with an NFC read module, using which a suitable transponder on the other component can be read out, if this transponder is located in the vicinity of the NFC read module.

Both components can each have an NFC read module and a transponder. In this case, a mutual readout of items of information of the transponder of the respective other component is possible, which can then be used at least to initiate the coupling.

Independently of whether only one or both components have an NFC read module, the items of information read out from the transponder of the respective other component can be at least sufficient to initiate a coupling. However, it is also possible that the items of information exchanged in this case can be sufficient to complete the coupling of the components immediately.

If it is sufficient, for example, for the unique assignment of control signals of a foot switch by a receiver that its unique identification and/or the public signature key is known to the receiver and if these items of information are completely contained on the transponder to be read out by the NFC read module, the coupling can already be completed solely on the part of the receiver after the readout of the items of information by the transponder and processing. The items of information on the transponder can also contain more detailed data on the component on which the transponder is arranged, on the basis of which the other component can check the compatibility and can prevent the coupling in the case of a negative result.

Alternatively, the mentioned items of information can be used to establish a data connection between the foot switch and the receiver, via which, for example, firstly a socalled handshake is carried out, in which possible encryption algorithms are negotiated or the mutual compatibility of the foot switch and the receiver is checked, before the two components are actually coupled to one another.

Even if a coupling takes place solely on the basis of the items of information read out by the transponder, the coupling can be verified once again by a corresponding data connection.

If only one NFC read module is provided for reading out a transponder in the vicinity, it can be arranged on the receiver and the foot switch has the transponder that can be read out by the NFC read module. A corresponding arrangement can be advantageous for the above-described complete coupling solely on the basis of items of information read out from the transponder.

The vicinity at which the NFC read module can read out a transponder can comprise a maximum distance between transponder and read device of 10 cm, such as 5 cm. A unique coupling which cannot be overheard between the foot switch and the receiver is possible by way of a correspondingly short distance.

To prevent a coupling from taking place inadvertently, the NFC read module or modules can be deactivated in the base state and can be activatable for coupling. If a coupling is desired, an NFC read module can be activated only temporarily—namely for the actual coupling. Inadvertently coupling a foot switch by unintentionally moving it toward an NFC read module can thus be avoided.

The receiver can be connected to an interface of the medical device suitable for this purpose, for example to an interface provided for a wired foot switch. The receiver and/or an NFC read module possibly assigned to the receiver can be integrated into the medical device to be controlled. Due to the simple free coupling ability achieved of a foot switch to a receiver, the external arrangement of receivers known from the prior art, to which a foot switch is practically permanently assigned and which can be connected to various medical devices, is no longer necessary. The NFC read module can be integrated spatially separated from the actual receiver in the medical device, in order to enable simpler coupling. For example, the NFC receiver can be arranged on the front side of the medical device, while the receiver is arrangeable at any other point inside the device.

The transponder can be an RFID transponder, which can be passive. Corresponding transponders do not require a separate energy source, but rather receive the energy required for reading out the items of information stored thereon from the electromagnetic field in the vicinity of an NFC read module.

The medical device to be controlled can be an HF generator, such as those configured for use in endoscopy, an ultrasound generator, and/or a laser system.

Although the explanations of the system fundamentally relate to the coupling of a foot switch and a receiver, it is immediately apparent that in the system, free coupling of any one of multiple foot switches to any one of multiple receivers is possible.

Reference is made to the above statements for the explanation of a corresponding method.

BRIEF DESCRIPTION OF THE DRAWINGS

The embodiments will be described as an example with reference to the appended schematic drawings. In the figures:

FIG. 1 illustrates an exemplary embodiment of a system; and

FIG. 2 illustrates the system from FIG. 1 during the coupling.

DETAILED DESCRIPTION

A system 1 according to an embodiment is shown in FIG. 1, in which a medical device 2, namely an HF generator 2 for an endoscopic resection tool 3, is controlled via a foot switch 10.

The foot switch 10 is wirelessly connected to the medical device 2 here. For this purpose, the medical device 2 has an integrated receiver 20, which is configured to receive control signals 90 emitted by the foot switch 10. The control signals 90 received by the receiver 20 are converted by the receiver 20 or another component of the medical device 2 after a positive check directly by the medical device 2.

The control signals 90 also comprise, in addition to the actual control commands, a unique identification 91, via which the control signals 90 can be uniquely assigned to a specific foot switch 10, namely the one shown in FIG. 1. The check of the control signals 90 received by the receiver 20 comprises the check of the identification 91 contained in the control signals 90. In this case, only the control commands of those control signals 90 are to be processed and ultimately implemented which originate from a predetermined foot switch 10. Such a one-to-one assignment of a specific foot switch 10 to a medical device 2 or its receiver 20 takes place in the context of the coupling of foot switch 10 and receiver 20.

For just this coupling, the receiver 20 comprises an NFC read module 21. Although the NFC read module is arranged spatially separate from the receiver 20 in the illustrated exemplary embodiment, by integrating both the receiver 20 and also the NFC read module 21 in the same medical device 2, a unique assignment is given between NFC read module 21 and receiver 20, so that the NFC read module 21 can be considered to be part of the receiver 20.

The NFC read module 21 is configured to read out items of information from a suitable transponder 11 located within the vicinity 22 having a radius of approximately 10 cm around the NFC read module 21. In the normal state, the NFC read module 21 is deactivated, but can be activated by a user for a short time period of approximately 10 seconds for the coupling.

The transponder 11, which can be read out in principle by the NFC read module 21, is arranged on the foot switch 11. The transponder 11 is a passive RFID transponder, in which at least the identification 91 of the foot switch 10 is stored.

To couple the foot switch 10 to the receiver 20 or the medical device 2, the NFC read module 21 is activated and the foot switch 10—as shown in FIG. 2—is brought into the vicinity of the medical device 2 in such a way that the transponder 11 of the foot switch 10 is located in the vicinity 22 of the NFC read module 21. It is then necessary to wait until the read module 21 has read out all items of information from the transponder 11, in which at least the unique identification 91 of the foot switch 10 is contained.

In the illustrated exemplary embodiment, the coupling of foot switch 10 and receiver 20 or the medical device 2 is already completed by reading out the unique identification 91 of the foot switch 10 by way of the NFC read module 21. From the point in time of this readout, the receiver 20 or the medical device 2 exclusively processes received control signals 90, which contain this same unique identification 91 (cf. FIG. 1).

However, it is also possible that the read out items of information are used in order to establish an initial wireless bidirectional connection between receiver 20 and foot switch 10, via which still further items of information, for example items of encryption information, are then exchanged before the coupling is actually completed and control signals 90 can be processed as described. These additional items of information can alternatively also be exchanged via an NFC arrangement, in which the foot switch 10 also has an NFC read module, which can then read out a transponder assigned to the receiver 20.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A system comprising:
a foot switch for controlling a medical device; and
a receiver for controlling the medical device;
wherein the foot switch and the receiver are configured for wirelessly transmitting uniquely assignable control signals after completion of mutually coupling the foot switch to the receiver and the receiver to the foot switch;
the foot switch and the receiver each have an NFC read module and a transponder and are each configured to initiate the mutual coupling when within a vicinity of each other by way of items of information mutually read out from the transponders;
the items of information read out from the transponder are sufficient to immediately complete the mutual coupling of the foot switch to the receiver and the receiver to the foot switch.

2. The system as claimed in claim 1, wherein the foot switch and the receiver are each configured to carry out and/or verify the coupling after reading out the items of information from the transponders by way of data exchange via a bidirectional wireless connection between foot switch and receiver.

3. The system as claimed in claim 1, wherein the vicinity comprises a maximum distance of 10 cm.

4. The system as claimed in claim 1, wherein the vicinity comprises a maximum distance of 5 cm.

5. The system as claimed in claim 1, wherein the NFC read module is deactivated in a base state and is activatable for the coupling.

6. The system as claimed in claim 1, wherein one or more of the receiver and the NFC read module is integrated into the medical device to be controlled.

7. The system as claimed in claim 1, wherein the transponder is an RFID transponder.

8. The system as claimed in claim 7, wherein the RFID transponder is passive.

9. The system as claimed in claim 1, wherein the medical device to be controlled is selected from a listing consisting of an HF generator an ultrasound generator, and a laser system.

10. A method for coupling a foot switch for controlling a medical device and a receiver connected to the medical device to be controlled according to the system as claimed in claim 1, the method comprising:
initiating the coupling between the foot switch and the receiver by moving the foot switch toward the receiver so that the transponder of the foot switch and the receiver is in the vicinity of the corresponding NFC read module of the foot switch and the receiver; and
waiting until the items of information required for the mutual coupling are exchanged and the mutual coupling is immediately completed.

* * * * *